United States Patent [19]

Jenkins

[11] Patent Number: 5,166,180

[45] Date of Patent: Nov. 24, 1992

[54] METHOD OF TREATING HEMATOLOGIC DISEASES AND PHARMACEUTICAL COMPOSITION TO BE USED THEREFOR

[75] Inventor: Vernon K. Jenkins, Houston, Tex.

[73] Assignee: Duphar International Research B.V., Weesp, Netherlands

[21] Appl. No.: 485,822

[22] Filed: Feb. 27, 1990

Related U.S. Application Data

[63] Continuation of Ser. No. 295,756, Jan. 11, 1989, abandoned, which is a continuation-in-part of Ser. No. 141,848, Jan. 11, 1988, abandoned.

[51] Int. Cl.$^5$ .................. A01N 47/28; A61K 31/17
[52] U.S. Cl. ...................................................... 514/594
[58] Field of Search ............................. 514/594, 544

[56] References Cited

U.S. PATENT DOCUMENTS

| | | | |
|---|---|---|---|
| 4,677,111 | 6/1987 | Haga et al. | 514/247 |
| 4,845,093 | 7/1989 | Haga et al. | 514/247 |
| 4,863,924 | 9/1989 | Haga et al. | 514/247 |
| 4,994,227 | 2/1991 | Dietz et al. | 264/328.16 |

FOREIGN PATENT DOCUMENTS

| | | | |
|---|---|---|---|
| 0107214 | 5/1984 | European Pat. Off. | |
| 0193249 | 9/1986 | European Pat. Off. | 514/594 |

Primary Examiner—Nathan M. Nutter
Attorney, Agent, or Firm—Stevens, Davis, Miller & Mosher

[57] ABSTRACT

The present invention relates to a method of treating hematopoietic diseases in warm-blooded living beings. The method is carried out by administering an effective amount of a compound of the formula

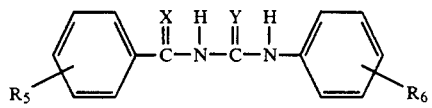

wherein $R_5$ represents (a) 1-3 substituents selected from the group consisting of halogen, $C_1$-$C_6$ alkyl, trifluoromethyl, $C_1$-$C_4$ alkoxy, $C_1$-$C_4$ alkylthio, hydroxy, $C_2$-$C_5$ alkanoyloxy, amino, N, N-di($C_1$-$C_4$) alkylamino and piperidyl; or (b) five fluorine atoms;

$R_6$ represents 1-3 substituents selected from the group consisting of halogen, $C_1$-$C_4$ alkyl, trifluoromethyl, $C_1$-$C_4$ alkoxy, $C_1$-$C_4$ haloalkoxy, cyclohexyloxy, adamantyloxy, hydroxy, amino and N-$C_2$-$C_5$ alkanoylamino;

X is oxygen or sulphur, and
Y is oxygen or sulphur.

4 Claims, No Drawings

METHOD OF TREATING HEMATOLOGIC DISEASES AND PHARMACEUTICAL COMPOSITION TO BE USED THEREFOR

REFERENCE TO RELATED APPLICATIONS

This application is a continuation of application Ser. No. 295,756, filed Jan. 11, 1989 and now abandoned, which in turn is a continuation-in-part of application Ser. No. 141,848, filed Jan. 11, 1988 and now abandoned.

BACKGROUND OF THE INVENTION

The present invention relates to a method of treating hematologic diseases in a warm-blooded living being.

Hematologic diseases, including immunodeficiency, anemia, result from a deficiency or defect in the capacity of the bone marrow cells to support hematopoiesis or in the ability of the living being to regulate production of blood cells. Means to regulate, support or enhance repopulation of bone marrow cells have been of interest for several decades, but satisfactory methods of regulation are still unavailable. Early research on hematopoietic stimulation (or repopulation) was related to efforts to rescue experimental animals from radiation-induced bone marrow suppression. Recent evidence that emphasizes the persistence of need for methods to regulate blood cell production was the futile attempt to rescue hematopoietically depressed victims of the Chernobyl nuclear power plant accident. It would be revolutionary to be able to regulate production of blood cells by the use of therapeutic agents. Such agents could have potential in treatment of patients with a broad range of diseases such as acquired immunodeficiency syndrome (AIDS) and AIDS related complex (ARC), including patients suffering from anemia, granulocytopenia or from immunodeficiency, (e.g., congenital, acquired or induced for organ transplantation). It must be emphasized that many years of diligent effort will be required to realize such a potential.

Consequently, there exists a long standing need for agents that have a potential to regulate or stimulate the production of blood cells, in particular of leukocytes, but also of lymphocytes, erythrocytes and blood platelets. Such agents would be therapeutic because many types of patients are hematologically suppressed and prone to infection. In fact many patients taking anti-cancer drugs suffer hematopoietic (and immunologic) suppression and may succumb to infectious diseases rather than cancer. Agents having a potential to regulate or stimulate blood cell production are considered therapeutically significant, not only in human medicine but also in veterinary science.

In order to asses hematopoietic effects the inventor has conducted studies on the influence of numerous agents on hematopoietic stem cells in an animal model system. As a result of such studies, it has now been found that certain amide compounds regulate or stimulate production of hematopoietic cells and, therefore, may be used for treating hematologic diseases.

Consequently the present invention relates to a method of treating hematologic diseases in warm-blooded living beings, comprising administering to the living being in an amount effective for regulating or stimulating hematopoiesis a composition comprising as the active substance at least one compound of the general formula

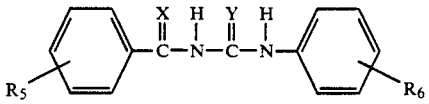

wherein
$R_5$ represents (a) 1-3 substituents selected from the group consisting of halogen, $C_1$-$C_6$ alkyl, trifluoromethyl, $C_1$-$C_4$ alkoxy, $C_1$-$C_4$ alkylthio, hydroxy, $C_2$-$C_6$alkanoyloxy, amino, N, N-di($CC_1$-$C_4$) alkylamino and piperidyl; or (b) five fluorine atoms;
X is an oxygen atom or a sulphur atom;
Y is an oxygen atom or a sulphur atom;
$R_6$ represents 1-3 substituents selected from the group consisting of halogen, $C_1$-$C_4$ alkyl, trifluoromethyl, $C_1$-$C_4$ alkoxy, $C_1$-$C_4$ haloalkoxy, cyclohexyloxy, adamantyloxy, hydroxy, amino and N-$C_2$-$C_5$ alkanoylamino.

The compounds to be used as active substances in the above compositions are partly known compounds, e.g. from European patent applications 25363, 107214, 164694, 166615, 169484, 178572, 192235 and 226104. In these patent publications an antitumor activity is demonstrated for the compounds disclosed, making them potentially valuable for the chemotherapeutic treatment of malignant tumors. It is generally known, however, that chemotherapeutic drug usually have a suppressive effect on blood cell production; see e.g. in this connection a recent article of Kulik and coworkers (Chem Abstr. 106, 1987, 188563). Therefore it is surprising, that the above-defined compounds show stimulating effects on hematopoietic stem cells and consequently offer an interesting potential for regulating or stimulating blood cell production.

In particular 1-(2,6-difluorobenzoyl)-3-(4-chlorophenyl)urea (1) and 1-(2-N,N-dimethylamino-6-fluorobenzoyl)-3-(4-chlorophenyl)urea (2) have proven to be highly suitable for achieving the intended effect.

Compounds which can be used as active substances for treating hematologic diseases in warm-blooded living beings are tabulated below: Tables E

TABLE E

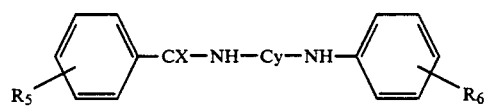

| comp. no. | $R_5$ | $R_6$ | X | Y |
|---|---|---|---|---|
| 1 | 2,6-$F_2$ | 4-Cl | O | O |
| 2 | 2-F, 6-N(CH$_3$)$_2$ | 4-Cl | O | O |
| 3 | 2,6-$F_2$ | 4-$CF_3$ | O | O |
| 4 | 2-F, 6-(1-piperidyl) | 4-$CF_3$ | O | O |
| 5 | 2-F, 6-N(CH$_3$)$_2$ | 4-OCF$_2$.CHF$_2$ | O | O |
| 6 | 2-Cl, 6-OH | 4-Cl | O | O |
| 7 | 2,3,4-(OH)$_3$ | 4-Cl | O | O |
| 8 | 2,6-$F_2$ | 4-O-(1-adamantyl) | O | O |
| 9 | 2-OCH$_3$, 6-N(CH$_3$)$_2$ | 4-Cl | O | O |
| 10 | 2-OCH$_3$, 6-N(CH$_3$)$_2$ | 3-$CF_3$ | O | O |
| 11 | 2-Cl, 6-SCH$_3$ | 3-$CF_3$, 4-OH | O | O |
| 12 | 2-OCH$_3$, 6-N(CH$_3$)$_2$ | 4-NH.CO.CH$_3$ | O | O |
| 13 | 2,6-(SCH$_3$)$_2$ | 4-Cl | O | O |
| 15 | 2-OCH$_3$, 6-N(CH$_3$)$_2$ | 4-OCF$_3$ | O | O |
| 16 | 4-$CF_3$ | 4-Cl | O | O |
| 17 | 2,6-$F_2$ | 3-Cl, 4-OH | O | O |
| 18 | 2,3,4,5,6-$F_5$ | 3-F, 4-Cl | O | O |
| 19 | 3,5-(OH)$_2$ | 4-Cl | O | O |
| 20 | 2,6-$F_2$ | 3,4,5-(OH)$_3$ | O | O |
| 21 | 2,4-(OH)$_2$ | 4-I | O | O |

TABLE E-continued

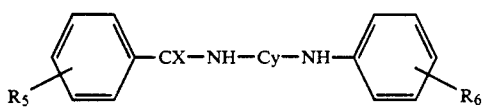

| comp. no. | R$_5$ | R$_6$ | X | Y |
|---|---|---|---|---|
| 22 | 3,4,5-(OH)$_3$ | 4-Cl | O | O |
| 23 | 4-NH$_2$ | 2-NH$_2$ | O | O |
| 24 | 2-Cl, 6-OH | 4-CF$_3$ | O | O |
| 25 | 2-F, 6-OH | 4-Cl | O | O |
| 26 | 2-NH$_2$ | 4-Cl | O | O |
| 27 | 2-F, 6-N(CH$_3$)$_2$ | 4-OCH$_3$ | O | O |
| 28 | 2-SCH$_3$ | 4-Cl | O | O |
| 29 | 2,3-(OH)$_2$ | 4-Cl | O | O |
| 30 | 3,4-(OH)$_2$ | 3,4-(OH)$_2$ | O | O |
| 31 | 4-Cl | 3,5-(t.butyl)$_2$, 4-OH | O | O |
| 32 | 2,6-F$_2$ | 3,5-Cl$_2$, 4-OCH$_2$CF$_3$ | O | O |
| 33 | 2-F | 4-Cl | O | O |
| 34 | 2,6-F$_2$ | 4-F | O | O |
| 35 | H | 4-Cl | O | O |
| 36 | 2,6-F$_2$ | 4-OCF$_2$CHFCl | O | O |
| 37 | 4-O.COCH$_3$ | 2-OH, 4-Cl | O | O |
| 38 | 2-OCH$_3$, 4-N(CH$_3$)$_2$ | 3-CF$_3$, 4-OH | O | O |
| 39 | 2-Cl, 4-NH$_2$ | 3,4-Cl$_2$ | O | O |
| 40 | 2-OCH$_3$, 6-N(CH$_3$)$_3$ | 3-Cl, 4-OH | O | O |
| 42 | 2,6-(OH)$_2$ | 4-Cl | O | O |
| 43 | 2,6-F$_2$ | 3-CF$_3$ | O | O |
| 44 | 2-SCH$_3$ | 4-Cl | O | S |
| 45 | 2-OH | 4-Cl | O | S |
| 46 | 3-Cl | 2-NH$_2$ | O | S |
| 47 | 2,6-F$_2$ | 4-Cl | O | S |
| 48 | 2-OCH$_3$ | 4-C$_2$H$_5$ | O | S |
| 49 | 2-OH | 4-Cl | S | S |
| 78 | 2,6-(CH$_3$)$_2$ | 4-Cl | O | S |
| 79 | 2,6-F$_2$ | 4-O-cyclohexyl | O | O |
| 80 | 2,6-F$_2$ | 2,3,4,5,6-F$_5$ | O | O |

Part of the above active compounds is new. The new compounds can be prepared in a manner known per se for related compounds. The new compounds of the present invention can be prepared by reacting a substituted amino compound of the general formula

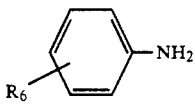

wherein R$_6$ has the above meaning,
with an iso(thio)cyanato compound of the general formula

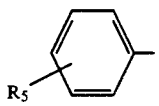

wherein R$_5$, X and Y have the above meanings.

The new compounds can also be prepared by reacting a (thio)amide of the general formula

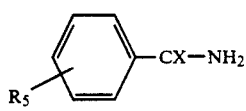

wherein R$_5$ and X have the above meanings,
with an iso(thio)cyanate of the general formula

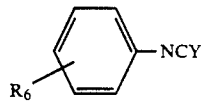

wherein R$_6$ and Y also have the above meanings.

The compounds obtained may be modified by an after-treatment to convert reactive side-chains like hydroxy, amino, etc. into functional derivatives such as alkoxy, N-alkylamino, N-acylamino, etc., and vice versa, to convert functional derivatives into the desired hydroxy, etc. substituted compounds.

The preparation of the new compounds is illustrated in the examples.

The present invention also relates to a pharmaceutical composition to be used for the method of treating hematologic diseases in warm-blooded living beings, comprising in addition to a pharmaceutically acceptable carrier and, if desired, at least one pharmaceutically acceptable adjuvant, as the active substance at least one compound as defined above in an amount effective for treating hematologic diseases. Such a composition may differ substantially from an antitumorous composition. Antitumorous compositions are usually administered repeatedly and therefore are given in relatively greater amounts, i.e. in maximally tolerated doses; such known compositions are generally administered intravenously by infusion, though oral administration is not excluded. The compositions of the present invention, however, are preferably in a form suitable for oral or rectal administration, e.g., in the form of tablets, pills, capsules, suppositories, etc., but may also be in a form suitable for intravenous or subcutaneous administration. In the compositions of the present invention the active substance is incorporated in a considerably lower dosage than for a chemotherapeutic substance.

The present invention further relates to a method of conventionally preparing a composition for treating hematologic diseases, that is, by incorporating the active substance in an amount effective for treating hematologic diseases into a pharmaceutically acceptable carrier, to which, if desired, at least one pharmaceutically acceptable adjuvant is added.

The hematopoietic stimulating activity of the compounds was determined in vivo, using animal model systems, and in vitro, using a culture of hematopoietic colonies.

The present invention will now be described in greater detail in the following Examples. It should be understood that these Examples are only intended to illustrate the present invention and not as a limitation thereof.

EXAMPLE I

Hematopoietic Stem Cell Response: in vivo experiment

| | abbreviations: |
|---|---|
| DFB = | 1-(2,6-difluorobenzoyl)-3-(4-chlorophenyl)urea |
| PVP = | polyvinylpyrrolidone |
| CFU$_s$ = | spleen colony forming unit |
| CSF = | colony stimulating factor |
| CFU = | colony forming unit |
| S.D. = | standard deviation |
| P = | statistical probability |
| BMC = | bone marrow cells |

| abbreviations: | |
|---|---|
| gm = | granulocytes + monocytes | a. Mice and irradiation. Ten-to-twelve-weeks-old mice of the C57B1/6 strain are used in these studies. Donor mice are treated with test drugs at different doses and schedules to induce changes in numbers of hematopoietic stem cells. Recipient mice are given 850 cGy (rad) total-body irradiation about two hours before bone marrow cell transplantation to reduce their endogeneous hematopoietic cells. Irradiation is delivered by a Philips 250 KVP X-ray machine operated at a target to source distance of 50 cm. 250 KV peak and 30 MA, 4.75 mm beryllium (Be) inherent filtration, 0.4 mm Thoraeus added filtration, and a dose rate of about 50 cGy/min.

b. Donor treatment. Selected drugs are injected into the donor mice at varied doses and schedules. The data reported below are from donors given a single dose (20 mg) of DFB 24 or 40 hours before sacrifice. Control mice are given an injection of 0.2 ml of 5% PVP.

c. Spleen colony technique. Donor mice are sacrificed, both femurs are removed, and the bone marrow cells are suspended in a cold balanced salt solution containing antibiotics. Counts of the bone marrow cells from individual donors are made in a hemocytometer and the numbers of cells per femur determined: Table A. In each experiment, cell suspensions from 5-10 donor mice within a drug-treatment or control group are combined and dilutions are made to obtain a concentration of $1 \times 10^5$ nucleated cells per ml. The cell suspensions are kept on ice until the time of injection into recipient mice, usually 1-2 hr after sacrifice of the donors. One-half ml of the cell suspension ($5 \times 10^4$ cells) from a drug-treatment or control group is injected into the tail vein of 5-10 irradiated (850 cGy) recipient mice. The recipients are sacrificed 8 days later and their spleens removed and fixed in buffered formalin.

The numbers of surface colonies (macroscopic) on the spleens are counted under a dissecting microscope after the spleens are stained in Bouin's solution for 10-15 min. The mean number of macroscopic colonies on spleens of groups of recipient mice are taken as the mean number of transplantable spleen colony forming units ($CFU_s$) contained in $5 \times 10^4$ bone marrow cells of the donor mice. The mean number of $CFU_s$ contained in each femur is determined by multiplying the mean number of $CFU_s$ per $5 \times 10^4$ cells by the mean number of bone marrow cells per femur of the donor-mouse groups. The results are presented in Table B.

After the numbers of surface colonies have been determined the spleens are embedded in paraffin and subserially sectioned (5 micrometers (mcm) thick sections at 125 mcm intervals) along the longitudinal axis for microscopic examination. The resulting sections are stained with hematoxylin and eosin and the numbers and cell type(s) of the colonies are tabulated: Table C. For an aggregate of cells to be called a colony, at least 20 cells are required in the largest cross section, except for megakaryocytic colonies which are counted if six cells are together. Colonies containing more than one cell type are considered mixed if the secondary cell type comprises an estimated 10% or more of the total cell number. Erythropoietic or granulocytic colonies contain pure cell lines with differing degrees of maturation. Undifferentiated colonies contain cells that are not matured enough to identify the line of differentiation for the cell type.

d. In vitro colony assay. Bone marrow cells are obtained from donor mice (treated and control) in the same manner as cells for the spleen colony technique.

Cell preparations for culture are made by adding $1 \times 10^6$ bone marrow cells (0.3 ml) to a 2% solution of methyl cellulose containing 8% fetal calf serum, 8% bovine serum albumin, 8% asparagine-thiol solution and 12.5% giant tumor cell conditioned medium. For each donor sample, $25 \times 10^4$ cells in one ml are added to each of three culture plates ($10 \times 35$ mm) and the plates are incubated at 37° C. in a mixture of 95% air/5% $CO_2$ for 7 days. The plates are then removed from incubation, cooled to arrest colony growth, and the number of colonies (CFUgm) per plate are counted under an inverted phase microscope. The number of CFUgm per donor femur is determined by multiplying the number of CFUgm per $25 \times 10^4$ cells by the number of cells per femur. The results are presented in Table D.

In addition to the studies with DFB, a composition with 1-(2-N,N-dimethylamino-6-fluorobenzoyl)-3-(4-chlorophenyl) urea as the active component is also tested in the same experimental models. The in vivo and in vitro effects of the second composition on CFU are similar to the effects produced by DFB.

TABLE A

| | NUMBER BONE MARROW CELLS PER FEMUR (C57BL/6 ♀) | | |
|---|---|---|---|
| TREATMENT | TIME AFTER TREATMENT | MEAN NUMBER OF CELLS ± S.D. × $10^6$/FEMUR | |
| 5% PVP (0.2 ml.) | 24 hours | 22.7 ± 4.1 | 8 femurs/4 animals |
| DFB (20 mg.) | 24 hours | 21.2 ± 4.4 | 9 femurs/5 animals |
| 5% PVP (0.2 ml.) | 40 hours | 20.5 ± 7.7 | 14 femurs/7 animals |
| DFB (20 mg.) | 40 hours | 19.2 ± 3.7 | 16 femurs/8 animals |

TABLE B

| MACROSCOPIC SPLEEN COLONIES (C57BL/6 ♀, 8 DAYS) | | | | |
|---|---|---|---|---|
| TREATMENT | TIME AFTER TREATMENT | NUMBER OF CELLS INJECTED | NUMBER OF COLONIES PER SPLEEN (NO. OF MICE) | NUMBER $CFU_s$ PER DONOR FEMUR |
| 5% PVP (0.2 ml.) | 40 hours | $5 \times 10^4$ | 7.4 ± 2.2 (19) | 2930 ± 851 |
| DFB (20 mg.) | 40 hours | $5 \times 10^4$ | 11.1 ± 3.1 (19)* | 3962 ± 672* |

*$P < 0.002$

TABLE C

| DONOR TREATMENT | TIME AFTER TREATMENT | NUMBER OF RECIPIENT MICE | MICROSCOPIC SPLEEN COLONIES ($5 \times 10^4$ BMC, C57BL/6 ♀) MEAN NUMBER OF COLONIES/SPLEEN SECTION (8 DAY) | | | | | | ERY./GRAN RATIO |
|---|---|---|---|---|---|---|---|---|---|
| | | | TOTAL | ERY. | GRAN. | UNDIFF. | MEG. | MIX. | |
| I { 5% PVP (0.2 ml.) | 40 hours | 8 | 10.8 | 5.2 (48%) | 2.8 (25%) | 2.2 (20%) | 0.73 (7%) | 0.10 (0.9%) | 1.8 |
| DFB (20 mg.) | 40 hours | 10 | 18.0 | 6.8 (38%) | 3.1 (17%) | 6.8 (38%) | 1.01 (6%) | 0.39 (2%) | 2.2 |
| II { 5% PVP (0.2 ml.) | 40 hours | 6 | 7.6 | 3.3 (43%) | 2.3 (30%) | 1.7 (22%) | 0.25 (3%) | 0.23 (3%) | 1.4 |
| DFB (20 mg.) | 40 hours | 6 | 8.3 | 2.3 (27%) | 1.8 (22%) | 3.4 (41%) | 0.85 (10%) | 0.10 (1%) | 1.3 |
| COMBINED I & II { 5% PVP (0.2 ml.) | 40 hours | 14 | 9.4 | 4.4 (47%) | 2.6 (28%) | 2.0 (21%) | 0.52 (5%) | 0.16 (2%) | 1.7 |
| DFB (20 mg.) | 40 hours | 16 | 14.4** | 5.1 (35%) | 2.6 (18%) | 5.5** (38%) | 0.95* (7%) | 0.28 (2%) | 2.0 |

*$P < 0.05$
**$P < 0.01$

TABLE D

| TREATMENT | TIME AFTER TREATMENT | IN VITRO BONE MARROW COLONIES (C57BL/6 ♀) MEAN NUMBER BM CELLS ± S.D. × $10^6$ PER FEMUR (NO. OF DONOR MICE) | MEAN NUMBER CFUgm ± S.D. PER $10^5$ CELLS (NO. OF PLATES) | MEAN NUMBER CFUgm ± S.D. PER FEMUR |
|---|---|---|---|---|
| 5% PVP (0.2 ml.) | 24 hours | 18.3 ± 4.6 (3) | 31.37 ± 3.28 (7) | 5710 ± 518 (7) |
| DFB (20 mg.) | 24 hours | 18.8 ± 8.0 (4) | 68.88 ± 14.4 (12)* | 12944 ± 1719 (12)* |
| 5% PVP (0.2 ml.) | 40 hours | 19.3 ± 5.7 (3) | 34.35 ± 2.6 (8) | 6602 ± 831 (8) |
| DFB (20 mg.) | 40 hours | 20.4 ± 2.2 (4) | 92.87 ± 21.7 (12)* | 18742 ± 2703 (12)* |

*$P = 0.0000$

EXAMPLE II

In vitro drug effects on $CFU_{gm}$

A murine bone marrow cell suspension is obtained by flushing the femurs of 7 week old B/CBA male mice with a sterile buffered salt solution. Clumps are dispersed by pushing them through a nylon sieve.

Cells are diluted to an end concentration of $5 \times 10^4$ cells/ml in Dulbecco's modified Eagle's medium supplemented with 20% (v/v) serum mixture of horse serum and foetal calf serum (2:1), L-asparagine and 0.3% (w//v) agar at a temperature of 40° C. Pregnant mouse uterus extract is added as a source of CSF.

Drugs (5 mg/ml DMSO) are diluted in the above described serum mixture and added to the culture at drug end concentrations as indicated below. One ml aliquots of the culture mixture are plated and solidified by incubation for 15 min. at 4° C. The cultures are subsequently incubated at 37° C. in a humidified atmosphere consisting of 10% $CO_2$ in air for 7 days. All determinations are performed in triplicate. Colonies larger than 50 cells are counted with an inverted microscope.

The results are compared with a blank consisting of a cell preparation incubated with solvent concentrations identical to those used in the experiments. If desired, dimethylformamide or polyvinylpyrrolidine is used as a solvent for the compound to be tested, instead of dimethylsulphoxide.

The following compounds (numbers as indicated before) show a significant increase in the number of colonies, even at a concentration of 0.03 μg per ml (percentage compared to blank in parentheses): 3 (129), 4 (146), 5 (127), 6 (131), 7 (134), 8 (141), 9 (141), 10 (141), 12 (135), 13 (147), 15 (127), 17 (142), 18 (132), 22 (128), 23 (134), 24 (158), 25 (131), 26 (128), 28 (132), 29 (147), 30 (144), 31 (147), 32 (135), 33 (137), 34 (130), 35 (140), 37 (135), 39 (146), 40 (130), 44 (136), 45 (130), 46 (135), 48 (138).

The following compounds show a significant increase in the number of colonies at a concentration of 0.1 μg per ml: 11 (144), 16 (137), 19 (130), 20 (127), 21 (131), 27 (126), 36 (126), 38 (131), 41 (136), 42 (138), 47 (128),

EXAMPLE III

In vivo drug effects on $CFU_{gm}$

To confirm the in vitro drug effects observed in Example II some selected drugs are tested for their in vivo activity.

Five-week old male B/CBA mice (2 mice/group) are intraperitoneally injected with 20 mg drug/20 g body weight suspended in 0.2 ml of a 5% solution of polyvinylpyrrolidone. After 40 hours the mice are killed by cervical dislocation and their femurs are disected. Bone marrow cell suspensions are prepared as described in Example II and the femoral cell content is determined. The number of $CFU_{gm}$ per $5 \times 10^4$ bone marrow cells is estimated as described in Example II and the number of $CFU_{gm}$ per femur is calculated. The following results, compared with the blank (5% polyvinylpyrrolidone) are obtained (in parentheses the factor with regard to the blank): 2 (2.31), 7 (2.02), 9 (2.70), 18 (1.83), 43 (2.63), 44 (2.27), 31 (2.77), 78 (3.60), 79 (2.96) and 80 (2.23).

EXAMPLE IV

Preparation of
1-(2-methylthiobenzoyl)-3-(4-chlorophenyl)urea (28)

2-Methylthiobenzamide in an amount of 1.67 g is suspended in 25 ml of dry xylene. After addition of 1.54 g of 4-chlorophenylisocyanate, the reaction mixture is refluxed over night. After cooling to room temperature the desired product crystallizes in a yield of 2.8 g, m.p. 211° C. The same result is obtained when 2-methylthiobenzoyl isocyanate is reacted with 4-chloroaniline.

In a corresponding manner, in which, if desired, instead of xylene diethyl ether or acetonitrile is used as a solvent, the following compounds are prepared; compound numbers correspond with the numbers given before:

| comp. no. | melt. point (°C.) |
|---|---|
| 4 | 125 |
| 5 | 101 |
| 31 | 228 |
| 42* | >280 |
| 48 | 93 |
| 78 | 191.5 |

*obtained from the corresponding 1-(2,6-dibenzyloxybenzoyl)-3-(4-chlorophenyl)urea by a reaction with HBr in acetic acid.

EXAMPLE V

Preparation of
1-(2-fluoro-6-hydroxybenzoyl)-3-(4-chlorophenyl)urea (25)

1-(2-Fluoro-6-methoxybenzoyl)-3-(4-chlorophenyl)urea, obtained by the method as described in Example IV, is suspended in an amount of 2.5 g in 35 ml of methylene chloride. Thereupon 2.27 ml of borium tribromide ($BBr_3$) in 15 ml of methylene chloride is added dropwise in a nitrogen atmosphere at −75° C. After stirring for 0.5 hour at −70° C. the reaction mixture is brought to room temperature. After stirring over night the reaction mixture is cooled again to −70° C. and 25 ml of methanol is added dropwise. After the reaction mixture is warmed up to room temperature the formed precipitate is sucked off and washed with methylene chloride. The title compound is obtained in a yield of 2.1 g; melting point 215° C.

In a corresponding manner the following compounds are prepared starting from the corresponding methoxy substituted compounds obtained according to Example IV. The compound numbers correspond again with the numbers given before in the specification:

| comp. no. | melt. point (°C.) |
|---|---|
| 7 | >250 |
| 19 | >240 |
| 20 | 214 |
| 21 | >250 |
| 22 | 233 |
| 29 | 206 |
| 30 | 250 |

EXAMPLE VI

Preparation of
1-(4-trifluoromethylbenzoyl)-3-(4-chlorophenyl)urea (16)

To a stirred solution of 1.08 g of 4-trifluoromethylbenzoylisocyanate in 5 ml of dry diethylether is added a solution of 0.64 g of 4-chloroaniline in 50 ml of acetonitrile. A precipitate is immediately formed. The precipitate is sucked off and washed with acetonitrile. The title compound is obtained a yield of 1.1 g; melting point 260° C.

In a corresponding manner, in which, if desired diethyl ether, acetonitrile or a mixture thereof is used as a solvent, the following compounds are obtained. For the required thiourea isothiocyanates are used as starting materials. The compound numbers corresponding again with the numbers given before:

| comp. no. | melt. point (°C.) |
|---|---|
| 8 | 222 |
| 11 | 229 |
| 17 | 194 |
| 18 | 237 |
| 37 | >260 |
| 79 | 186 |
| 47 | 191 |
| 80 | 188 |

EXAMPLE VIII

Preparation of
1-(2-chloro-4-aminobenzoyl)-3-(3,4-dichlorophenyl)urea (39)

1-(2-chloro-4-nitrobenzoyl)-3-(3,4-dichlorophenyl)urea, obtained by the method described in Example IV, is dissolved in an amount of 1.9 g in 20 ml of dimethylformamide and thereupon hydrogenated in the presence of $PtO_2$ as a catalyst for 24 hours. After separating the catalyst by suction, the filtrate is evaporated in vacuo and the residue boiled with isopropanol. After cooling down to room temperature the desired product is obtained in a yield of 1.5 g; melting point 280° C.

In a corresponding manner compound no. 46, having a melting point of 153° C., is obtained.

EXAMPLE IX

Preparation of
1-(2-chloro-6-hydroxybenzoyl)-3-(4-trifluoromethylphenyl)urea (24)

An amount of 2.2 g of 1-(2-chloro-6-benzyloxybenzoyl)-3-(4-trifluoromethylphenyl)urea, obtained by the method as described in Example VI, is dissolved in 20 ml of 48% hydrobromic acid in acetic acid. After stirring for 2.5 hours at 90° C. a precipitate is formed. The reaction mixture is cooled to room temperature and the precipitate is sucked off; the precipitate is washed successively with acetic acid and water. The title compound is obtained in a yield of 1.47 g; melting point 264° C.

In a corresponding manner the following compounds are obtained: compound no. 42, melting point >280° C., and compound no. 77, melting point 188° C.

EXAMPLE X

Preparation of
1-(2-methoxy-6-dimethylaminobenzoyl)-3-(3-trifluoromethylphenyl)urea (10)

1-(2-methoxy-6-fluorobenzoyl)-3-(3-trifluoromethylphenyl)urea is dissolved in an amount of 1.0 g in 6 ml of dimethylformamide. The starting compound is obtained by the method as described in Example VI. Liquified dimethylamine in an amount of 0.5 ml is added and the reaction mixture is heated on 100° C. for 4 hours in a sealed tube. After cooling down to room temperature the reaction mixture is poured on ice-water. The formed precipitate is filtered off and washed with water. The desired compound is obtained in a yield of 0.8 g; melting point 180° C.

In a corresponding manner the following compounds are obtained; the numbers correspond again with the numbers given before:

| comp. no. | melt. point (°C.) |
|---|---|
| 12 | 198 |
| 38 | 205 |
| 40 | 161 |

I claim:

1. A method for the treatment of warm-blooded living beings suffering from a hematologic disease selected from the class consisting of anemia, granulocytopenia and immunodeficiency, whether congenital, acquired or induced, or suffering from a disease resulting from said hematologic disease, comprising administering to a living being suffering from said disease, in an amount effective for regulating or stimulating hematopoiesis, a composition comprising as the active substance at least one numbered compound selected from the class consisting of those having the formula

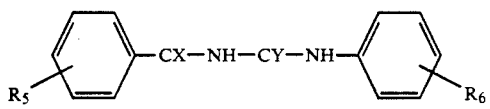

wherein the substituents $R_5$, $R_6$, X and Y have the following meanings:

| comp. no. | $R_5$ | $R_6$ | X | Y |
|---|---|---|---|---|
| 1 | 2,6-$F_2$ | 4-Cl | O | O |
| 2 | 2-F, 6-N($CH_3$)$_2$ | 4-Cl | O | O |
| 3 | 2,6-$F_2$ | 4-$CF_3$ | O | O |
| 4 | 2-F, 6-(1-piperidyl) | 4-$CF_3$ | O | O |
| 5 | 2-F, 6-N($CH_3$)$_2$ | 4-$OCF_2.CHF_2$ | O | O |
| 6 | 2-Cl, 6-OH | 4-Cl | O | O |
| 7 | 2,3,4-(OH)$_3$ | 4-Cl | O | O |
| 8 | 2,6-$F_2$ | 4-O-(1-adamantyl) | O | O |
| 9 | 2-$OCH_3$, 6-N($CH_3$)$_2$ | 4-Cl | O | O |
| 10 | 2-$OCH_3$, 6-N($CH_3$)$_2$ | 3-$CF_3$ | O | O |
| 11 | 2-Cl, 6-$SCH_3$ | 3-$CF_3$, 4-OH | O | O |
| 12 | 2-$OCH_3$, 6-N($CH_3$)$_2$ | 4-NH.CO.$CH_3$ | O | O |
| 13 | 2,6-($SCH_3$)$_2$ | 4-Cl | O | O |
| 14 | 2,6-$F_2$ | 4-[4-{N-(4-chlorophenyl)-carbamoyl}-piperazinyl(-1)] | O | O |
| 15 | 2-$OCH_3$, 6-N($CH_3$)$_2$ | 4-$OCF_3$ | O | O |
| 16 | 4-$CF_3$ | 4-Cl | O | O |
| 17 | 2,6-$F_2$ | 3-Cl, 4-OH | O | O |
| 18 | 2,3,4,5,6-$F_5$ | 3-F, 4-Cl | O | O |
| 19 | 3,5-(OH)$_2$ | 4-Cl | O | O |
| 20 | 2,6-$F_2$ | 3,4,5-(OH)$_3$ | O | O |
| 21 | 2,4-(OH)$_2$ | 4-Cl | O | O |
| 22 | 3,4,5-(OH)$_3$ | 4-Cl | O | O |
| 23 | 4-$NH_2$ | 2-$NH_2$ | O | O |
| 24 | 2-Cl, 6-OH | 4-$CF_3$ | O | O |
| 25 | 2-F, 6-OH | 4-Cl | O | O |
| 26 | 2-$NH_2$ | 4-Cl | O | O |
| 27 | 2-F, 6-N($CH_3$)$_2$ | 4-$OCH_3$ | O | O |
| 28 | 2-$SCH_3$ | 4-Cl | O | O |
| 29 | 2,3-(OH)$_2$ | 4-Cl | O | O |
| 30 | 3,4-(OH)$_2$ | 3,4-(OH)$_2$ | O | O |
| 31 | 4-Cl | 3,5-(t.butyl)$_2$, 4-OH | O | O |
| 32 | 2,6-$F_2$ | 3,5-$Cl_2$, 4-$OCH_2CF_3$ | O | O |
| 33 | 2-F | 4-Cl | O | O |
| 34 | 2,6-$F_2$ | 4-F | O | O |
| 35 | H | 4-Cl | O | O |
| 36 | 2,6-$F_2$ | 4-$OCF_2CHFCl$ | O | O |
| 37 | 4-O.$COCH_3$ | 2-OH, 4-Cl | O | O |
| 38 | 2-$OCH_3$, 4-N($CH_3$)$_2$ | 3-$CF_3$, 4-OH | O | O |
| 39 | 2-Cl, 4-$NH_2$ | 3,4-$Cl_2$ | O | O |
| 40 | 2-$OCH_3$, 6-N($CH_3$)$_2$ | 3-Cl, 4-OH | O | O |
| 41 | 2,6-($SCH_3$)$_2$ | 4-$OC_6H_4$—$CF_3$-4 | O | O |
| 42 | 2,6-(OH)$_2$ | 4-Cl | O | O |
| 43 | 2,6-$F_2$ | 3-$CF_3$ | O | O |
| 44 | 2-$SCH_3$ | 4-Cl | O | S |
| 45 | 2-OH | 4-Cl | O | S |
| 46 | 3-Cl | 2-$NH_2$ | O | S |
| 47 | 2,6-$F_2$ | 4-Cl | O | S |
| 48 | 2-$OCH_3$ | 4-$C_2H_5$ | O | S |
| 49 | 2-OH | 4-Cl | S | S |
| 78 | 2,6-($CH_3$)$_2$ | 4-Cl | O | S |
| 79 | 2,6-$F_2$ | 4-O-cyclohexyl | O | O and |
| 80 | 2,6-$F_2$ | 2,3,4,5,6-$F_5$ | O | O |

2. A method for the treatment of warm-blooded living beings suffering from a hematologic disease selected from the class consisting of anemia, granulocytopenia and immunodeficiency, whether congenital, acquired or induced, or suffering from a disease resulting from said hematologic disease, comprising administering to a living being suffering from said hematologic disease, in an amount effective for regulating or stimulating hematopoiesis, a composition comprising as the active substance a compound selected from the class consisting of those having the formula

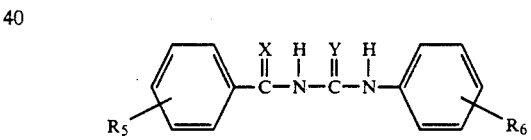

wherein
$R_5$ represents (a) 1-3 substituents selected from the group consisting of halogen, $C_1$-$C_6$ alkyl, trifluoromethyl, $C_1$-$C_4$ alkoxy, $C_1$-$C_4$ alkylthio, hydroxy, $C_2$-$C_5$ alkanoyloxy, amino, N,N-di($C_1$-$C_4$)alkylamino and piperidyl; or (b) five fluorine atoms;
$R_6$ represents 1-3 substituents selected from the group consisting of halogen, $C_1$-$C_4$ alkyl, trifluoromethyl, $C_1$-$C_4$ alkoxy, $C_1$-$C_4$ haloalkoxy, cyclohexyloxy, adamantyloxy, hydroxy, amino and N-$C_2$-$C_5$ alkanoylamino;
X is an oxygen atom or a sulphur atom; and
Y is an oxygen atom or a sulphur atom.

3. A method as claimed in claim 2, wherein the active substance is selected from the group consisting of 1-(2,6-difluorobenzoyl)-3-(4-chlorophenyl)urea and 1-(2-N,N-dimethylamino-6-fluorobenzoyl)-3-(4-chlorophenyl)urea.

4. A method as claimed in claim 2, wherein the active substance is 1-(2-N,N-dimethylamino-6-fluorobenzoyl)-3-(4-chlorophenyl)urea.

* * * * *